US009949701B2

(12) United States Patent
Meyer et al.

(10) Patent No.: US 9,949,701 B2
(45) Date of Patent: Apr. 24, 2018

(54) REGISTRATION FOR TRACKED MEDICAL TOOLS AND X-RAY SYSTEMS

(71) Applicants: Andreas Meyer, Bubenreuth (DE); Sebastian Schafer, Madison, WI (US)

(72) Inventors: Andreas Meyer, Bubenreuth (DE); Sebastian Schafer, Madison, WI (US)

(73) Assignee: Siemens Aktiengesellschaft, München (DE)

( * ) Notice: Subject to any disclaimer, the term of this patent is extended or adjusted under 35 U.S.C. 154(b) by 268 days.

(21) Appl. No.: 14/181,600

(22) Filed: Feb. 14, 2014

(65) Prior Publication Data

US 2014/0228678 A1    Aug. 14, 2014

Related U.S. Application Data

(60) Provisional application No. 61/764,768, filed on Feb. 14, 2013.

(51) Int. Cl.
| | |
|---|---|
| A61B 5/00 | (2006.01) |
| A61B 6/12 | (2006.01) |
| A61B 6/00 | (2006.01) |
| A61M 5/00 | (2006.01) |
| A61B 34/20 | (2016.01) |
| A61B 90/00 | (2016.01) |

(52) U.S. Cl.
CPC .............. *A61B 6/12* (2013.01); *A61B 6/466* (2013.01); *A61B 6/481* (2013.01); *A61B 6/485* (2013.01); *A61B 6/487* (2013.01); *A61B 6/5235* (2013.01); *A61B 34/20* (2016.02); *A61B 90/39* (2016.02); *A61M 5/007* (2013.01); *A61B 6/504* (2013.01); *A61B 2090/3966* (2016.02)

(58) Field of Classification Search
CPC ....... A61B 5/061; A61B 5/0084; A61B 5/064; A61B 8/12; A61B 6/5217; A61B 5/0066; A61B 5/0075; A61B 5/066
See application file for complete search history.

(56) References Cited

U.S. PATENT DOCUMENTS

| | | | |
|---|---|---|---|
| 7,048,716 B1 * | 5/2006 | Kucharczyk ...... | A61M 25/0043 600/411 |
| 2004/0171924 A1 * | 9/2004 | Mire .................... | G06F 19/3437 600/407 |
| 2008/0208039 A1 * | 8/2008 | Kurpad .................... | A61B 5/06 600/424 |
| 2011/0038517 A1 * | 2/2011 | Mistretta .................. | A61B 6/02 382/128 |

(Continued)

*Primary Examiner* — Joel Lamprecht
(74) *Attorney, Agent, or Firm* — Lempia Summerfield Katz LLC

(57) ABSTRACT

In order to increase the accuracy of registration between a world coordinate system and an image coordinate system such that a tracked medical tool may be moved forward in the body of a patient without any additional or with limited live imaging, a method for registration of the tracked medical tool with an X-ray system is provided. The method includes receiving image data from the X-ray system at a plurality of time points, receiving tracking data from a tracking device of the tracked medical tool at the plurality of time points, and registering the world coordinate system and the image coordinate system based on the received image data and the received tracking data at the plurality of time points.

20 Claims, 12 Drawing Sheets

(56) References Cited

U.S. PATENT DOCUMENTS

2014/0094689 A1* 4/2014 Cohen .................. A61B 5/7425
600/424
2014/0314196 A1* 10/2014 Zou ........................ A61B 6/032
378/4

* cited by examiner

US 9,949,701 B2

REGISTRATION FOR TRACKED MEDICAL TOOLS AND X-RAY SYSTEMS

This application claims the benefit of U.S. Provisional Application No. 61/764,768, filed on Feb. 14, 2013, the disclosure of which is incorporated herein.

FIELD

The present embodiments relate to registration for tracked medical tools and X-ray systems.

BACKGROUND

Electromagnetic tracking may be provided in a number of medical applications. A path for a medical tool may be planed, the path may be overlaid over an image, and the medical tool may be tracked along the path. This tracking may be used for inserting a medical device (e.g., a needle) for biopsy or local treatment of a tumor. The tracking may be visualized using a volumetric pre-operation dataset such as a magnetic resonance (MR) dataset or a computed tomography (CT) dataset.

Electromagnetic tracking may also be provided for the guidance of intravascular devices such as, for example, catheters and guidewires. Pre-operation or intra-operation three dimensional (3D) images may be used as a 3D roadmap. An operator of the catheter, for example, may follow a planned path or a vessel along the 3D roadmap. The operator is to know where an actual position of the catheter is as the catheter is moved within the body of a patient. The actual position of the catheter may be obtained from one or more coils integrated into the catheter, for example. The one or more coils are tracked by an electromagnetic tracking system.

The electromagnetic tracking system knows a position of the one or more coils integrated into the catheter in a coordinate system of the electromagnetic tracking system (e.g., a world coordinate system). The electromagnetic tracking system, however, does not know the position of the one or more coils integrated into the catheter in a coordinate system (e.g., an image coordinate system) of a pre-operation scan (e.g., an MR dataset or a CT volumetric dataset) or an intra-operation scan (e.g., a 3D angiographic dataset or a DynaCT dataset).

If registration between the world coordinate system and the image coordinate system is achieved with a high enough degree of accuracy, and the morphological situation during an intervention does not change, the catheter, for example, may be moved forward in the body of the patient without any additional live imaging (e.g., fluoroscopy or ultrasound).

In one example in the prior art, registration between the world coordinate system and the image coordinate system is provided by fixing the mechanical relationship between an angiographic X-ray system and an Electromagnetic tracking system in combination with a calibration of the geometry of the angiographic X-ray system. In another example in the prior art, the registration between the world coordinate system and the image coordinate system is provided by a reference frame, which is visible in a volume of interest, including reference markers (e.g., fiducials) in a fixed relationship to a reference coil system.

SUMMARY

In order to increase the accuracy of registration between a world coordinate system and an image coordinate system such that a tracked medical tool may be moved forward in the body of a patient without any additional or with limited live imaging, a method for registration of the tracked medical tool with an X-ray system is provided. The method includes receiving image data from the X-ray system at a plurality of time points, receiving tracking data from a tracking device of the tracked medical tool at the plurality of time points, and registering the world coordinate system and the image coordinate system based on the received image data and the received tracking data at the plurality of time points.

In a first aspect, a method for registration of an endovascular device with an X-ray system is provided. The endovascular device includes a tracking device. The method includes receiving image data from the X-ray system at a plurality of time points. The image data includes image data representing at least a portion of the endovascular device in a first coordinate system as the endovascular devices moves within or through the first coordinate system. Tracking data is received from the tracking device at the plurality of time points. The tracking date represents a position of the endovascular device in a second coordinate system. A processor registers the second coordinate system with the first coordinate system based on the received image data and the received tracking data at the plurality of time points.

In a second aspect, a system for registration of a tracked tool with an X-ray system is provided. The tracked tool includes a tracking device. The system includes an X-ray system configured to generate image data representing at least a portion of the tracked tool in a first coordinate system as the tracked tool moves within or through the first coordinate system. The system also includes a processor configured to receive tracking data from the tracking device while the X-ray system generates the image data. The tracking data represents a position of the tracked tool in a second coordinate system. The processor is also configured to register the second coordinate system with the first coordinate system based on the received image data and the received tracking data.

In a third aspect, a non-transitory computer-readable storage medium that stores instructions executable by one or more processors for registration of data generated by a tracked medical tool with image data generated by an X-ray system is provided. The tracked medical tool includes a tracking device. The instructions include receiving image data from the X-ray system at a plurality of time points. The image data includes image data representing at least a portion of the tracked medical tool in a first coordinate system as the tracked medical tool moves within or through the first coordinate system. The instructions also include receiving tracking data from the tracked medical tool at the plurality of time points, the tracking data representing a position of the tracked medical tool in a second coordinate system. The instructions include registering the second coordinate system with the first coordinate system based on the received image data and the received tracking data at the plurality of time points.

BRIEF DESCRIPTION OF THE DRAWINGS

The components and the FIGS. are not necessarily to scale. Emphasis instead is placed on illustrating the principles of the invention. In the FIGS., like reference numerals designate corresponding parts throughout the different views.

DETAILED DESCRIPTION

Figure 1:
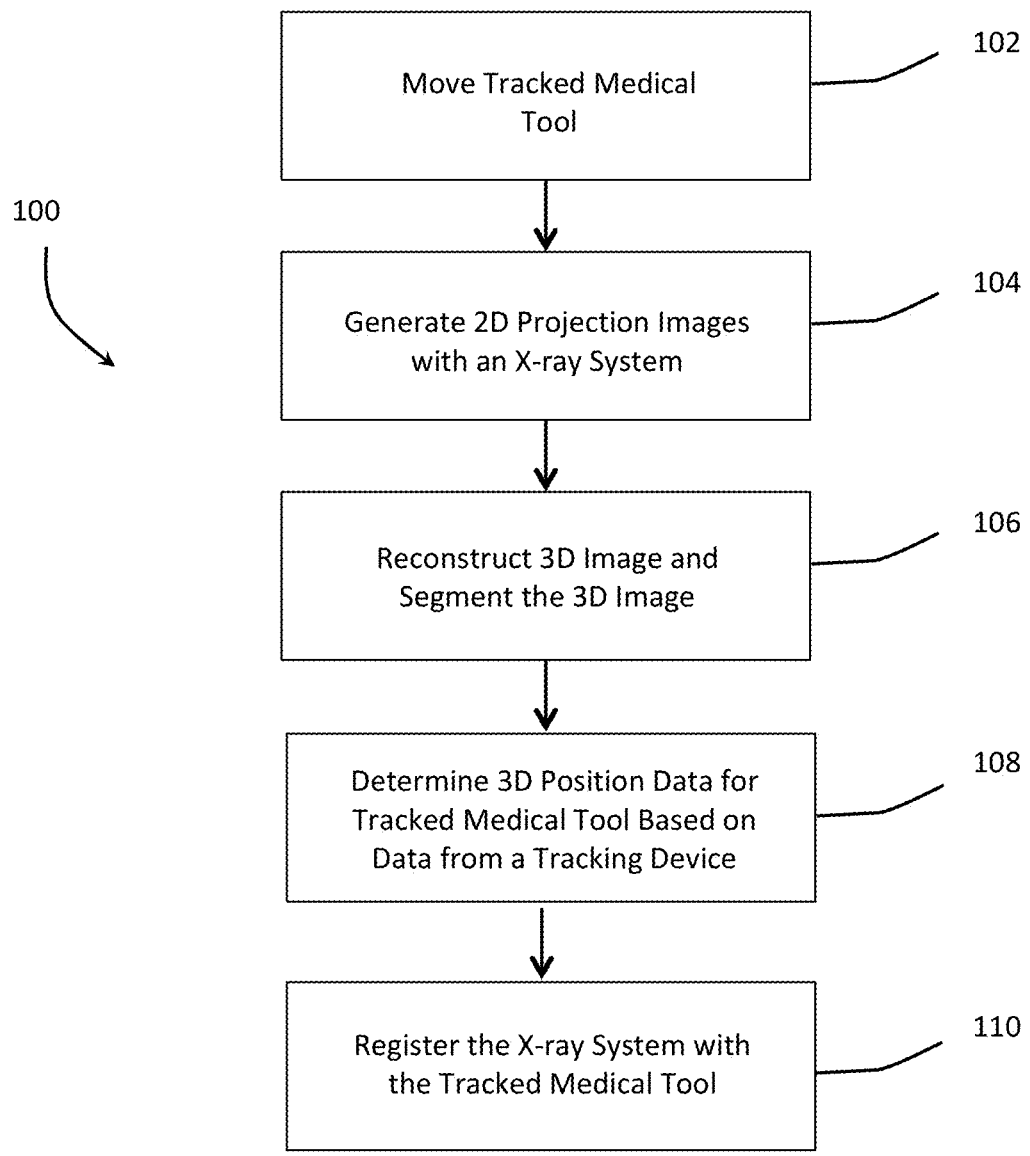
FIG. 1 is a flow chart diagram of a first embodiment of a method for registering a tracked medical tool and an imaging system.

A system is provided for performing methods of registration for tracked endovascular tools and X-ray systems (e.g., cone-beam systems) with known geometry. The system includes, for example, a tracked endovascular tool (e.g., a guidewire or a catheter) with distinct markers or tracking markers (e.g., tracking coils, RFID chips, or center-of-mass representing fiducials). One or more of the tracking markers are visible in X-ray projections. The system also includes an X-ray system with available geometric data for distinct projection views.

For three dimensional (3D) registration with determined points and multiple tracking markers, the tracked tool is moved into a cone-beam system field of view. A number, n, of projection images (e.g., two or more projection images) are acquired. For each of the projection images, the imaging system geometry is known. Simultaneously, positions of one or more tracking markers of the tracked tool are recorded. A 3D image reconstruction is performed from the acquired projection images, and the one or more tracking markers are segmented from the 3D image reconstructions. For 3D reconstruction of a tracking marker after segmentation in two dimensions, if the vector paths do not intersect, a 3D point with a minimal distance to all vector paths is calculated and taken as a best approximation of the 3D tracking marker position in an image domain (e.g., 3D image coordinate system). Alternatively, the one or more tracking markers may be segmented from the projection images, and 3D positions may be reconstructed from the segmented projection images. The positions may be determined without segmentation.

With the tracked marker positions calculated for the 3D image coordinate system, corresponding 3D tool positions are collected in the world coordinate system from, for example, a tracking controller. The 3D tool positions may be an average position of the tracking marker during image acquisition. Point based registration is performed between the tracked marker positions and the corresponding 3D tool positions.

For 3D registration without determined points but with self-calibration and multiple markers, the tracked tool is moved into a cone-beam X-ray system field of view. A number of projection images, n, are acquired. For each of the projection images, the X-ray system geometry is known. A 3D image reconstruction is performed from the acquired projection views. The target of the 3D image reconstruction is to visualize the tracked tool. Filtering may be applied to isolate the tracked tool in the projection images.

The tracked tool is segmented from the 3D image reconstruction. 3D positions of tracking markers of the tracked tool in the world coordinate system are collected from a tracking device of the tracked tool. A most distal and a most proximal tracked marker position may be determined using, for example, a specific ID for each of the tracking markers. The 3D shape of the tracked tool in the 3D image reconstruction may be matched and/or fit to the 3D positions of the tracking markers of the tracked tool in the world coordinate system. Locations where the tracking marker position and the 3D shape coincide/are closest may be used as registration points.

Because error sources such as large metallic devices and even the human body may disturb the magnetic field, a self-calibration procedure may also be provided. A least squares match of a shape to the tracked marker positions may be determined. Assuming the distortion caused by the error sources is homogenous throughout the tracked tool, 3D correction vectors are determined for each of the tracked marker positions. The determined correction is then applied to the tracked marker positions during tracking. The correction vectors may be extrapolated throughout the trackable volume (e.g., the tracked tool).

If only one trackable marker is available on the tracked tool, a 3D digital subtraction angiography (DSA) and biplane fluoroscopy may be used. A 3D DSA is acquired. The tracked tool is advanced to a position visible in a biplane imaging system FOV. The position of the patient may change, but the tracked tool is to be positioned in the 3D DSA structure (e.g., using a 3D/2D overlay of the reconstructed data on the fluoroscopic projection data).

Fluoroscopic images of the moving tracked tool are acquired in two planes (e.g., a vertical plane and a horizontal plane) using roadmap functionality. Simultaneously, the position of the trackable marker is recorded. For each such acquired image pair and corresponding tracked tool position, a 3D position of the tracked tool or the trackable marker is triangulated within the 3D DSA.

If the trackable marker position is clearly visible and has been extracted in the fluoroscopic images, the corresponding triangulated 3D position may be used for registration. If the trackable marker position is not clearly visible, the known shape of the tracked tool (e.g., with marker position) may be fit to the reconstructed/triangulated tracked tool, and the tracking marker position may be correlated. Fitting may include a constraint deformation of the tracked tool (e.g., from a starting point of a straight line to the reconstructed shape).

With this correspondence established for all of the acquired image pairs and trackable marker positions, point based registration is used to correlate the image coordinate system with the world coordinate system.

If only one trackable marker is available on the tracked tool, the 3D digital subtraction angiography (DSA) may also be used with monoplane fluoroscopy. A 3D DSA may be acquired with the tracked tool (e.g., a guidewire) including an electromagnetic (EM)-trackable marker in the field of view. A 3D native mask image (e.g., a non-contrast scan) and a 3D DSA image of vasculature are reconstructed.

The trackable marker is extracted in the native mask 3D reconstruction (e.g., in the image coordinate system), and the extracted representation of the marker is matched with the position of the EM tracked marker position (e.g., in the world coordinate system). A representation of the tracked tool is also extracted from the native mask 3D reconstruction, and the tool diameter in the representation of the tracked tool is increased (e.g., by blurring or in-plane diameter dilation), thus providing an altered representation of the tracked tool. Fluoroscopic images of the moving tool are acquired (e.g., in a roadmap) while the tracking position of the trackable marker is simultaneously recorded.

The moving tracked tool is backprojected (e.g., a backprojected 2D object) into the 3D using the altered representation of the tracked tool as a constraining volume. If the EM-trackable marker may be recognized/segmented in the fluoroscopic image, only a representation of the EM-trackable marker may be backprojected.

A 3D image coordinate of the moving tracked tool is determined as an intersection point of the backprojected 2D object and the altered 3D representation of the tracked tool. If there is more than one intersection coordinate for the tracked tool, as well as the trackable marker, the center of mass may be used as a first approximation of the tool/marker position.

The recorded 3D point pairs, the intersecting 2D fluoroscopic backprojections, and the simultaneously recorded tracking positions for the trackable marker may be used as a basis for a point based image to world coordinate system registration, calibration, or transformation.

If only one trackable marker is available on the tracked tool, a 3D DSA may be used alone. A tracked tool may be moved into a field of view of a 3D DSA image acquisition, high enough into a vasculature of a patient, for example, to allow distal movement of the tracked tool with the field of view. The tracked tool may not overlay any vasculature of interest.

A 3D mask run is acquired during pull-back of the tracked tool. For each acquired projection image, world coordinates for the tracked tool (e.g., the trackable marker of the tracked tool) are recorded. A 3D fill run is also acquired.

A 3D DSA and a 3D image from the acquired native mask run are reconstructed. The native mask will include a blurred reconstruction of the tracked tool due to the motion during the reconstruction. For each acquired projection image in the native mask run (e.g., with the tracked tool moving from frame to frame), the tracked tool is extracted (e.g., segmented) and backprojected into 3D.

An intersection of the backprojected tool and the blurred 3D reconstruction is determined. If the trackable marker is clearly visible in the projection image (e.g., the two dimensional (2D) projection image, a 3D intersection coordinate is determined. If the trackable marker is not visible, knowledge of the position with respect to the tool shape is used to determine the position in 3D. If there are more than one intersection coordinate for the tracked tool, as well as the trackable marker, the center of mass may be used as a first approximation of the tool/marker position.

With the 3D marker position determined for each acquisition frame, the simultaneously recorded tracking marker position is used to establish image-to-world coordinate system registration.

FIG. 1 is a flow chart diagram of an embodiment of a method 100 for registering a tracked medical tool and an imaging system. The tracked medical tool may be, for example, a tracked endovascular tool such as a guidewire or a catheter. The tracked medical tool may include two or more tracking markers. The two or more tracking markers may be visible in an image generated by the imaging system, and each tracking marker of the one or more tracking markers may include a tracking device. The tracking device may include, for example, a tracking coil or an RFID chip. The tracking coil, for example, may generate an electromagnetic (EM) signal, and the generated EM signal may be read out by a processor (e.g., a processor separate from the tracking coil). The processor may determine a global position of the tracking marker (e.g., within a global coordinate system) based on the read out EM signal generated by the tracking coil. Other tracking devices may be provided. The same tracking marker is both detectable from data of an imaging system and useable for tracking. Alternatively, different devices on the same tool are used for each.

The imaging system may be any number of imaging systems. For example, the imaging system may be a cone-beam X-ray system. The cone-beam X-ray system may be a C-arm X-ray system or may be a biplane X-ray system. The cone-beam X-ray system may generate two-dimensional projection images, fluoroscopic images, angiographic images, or any number of other types of images. Imaging systems other than X-ray imaging systems may also be used.

In act 102, the tracked medical tool is moved through a body of a patient into a field of view of the imaging system. In act 104, a number, n, of 2D projection images (e.g., two or more projection images) are generated by a processor of the imaging system. Image data is received from a detector of the imaging system, for example, and the processor generates the n 2D projection images based on the received image data. For each projection image of the n 2D projection images, the geometry of the imaging system is known. The imaging system may generate the n 2D projection images at different positions relative to the patient. For example, the imaging system may include a C-arm, and an X-ray source and a detector attached to different ends of the C-arm. The C-arm may be rotated around the patient, and the n 2D projection images are generated at different angles relative to the patient and thus the tracked medical tool.

In act 106, the processor reconstructs a 3D image from the n 2D projection images. In one embodiment, representations of the two or more tracking markers are segmented from and/or identified in the reconstructed 3D data or image. The representations of the two or more tracking markers may be automatically segmented from the reconstructed 3D data. Alternatively, a user of the imaging system may identify a region within the reconstructed image to be segmented using an input device, and the processor may segment the representation of the two or more tracking markers based on the identified region received from the input device. In another embodiment, representations of the tracking markers may be segmented from the n 2D projection images, and the segmented representations of the tracking markers may be reconstructed to identify 3D positions of the tracking markers.

Figure 2:
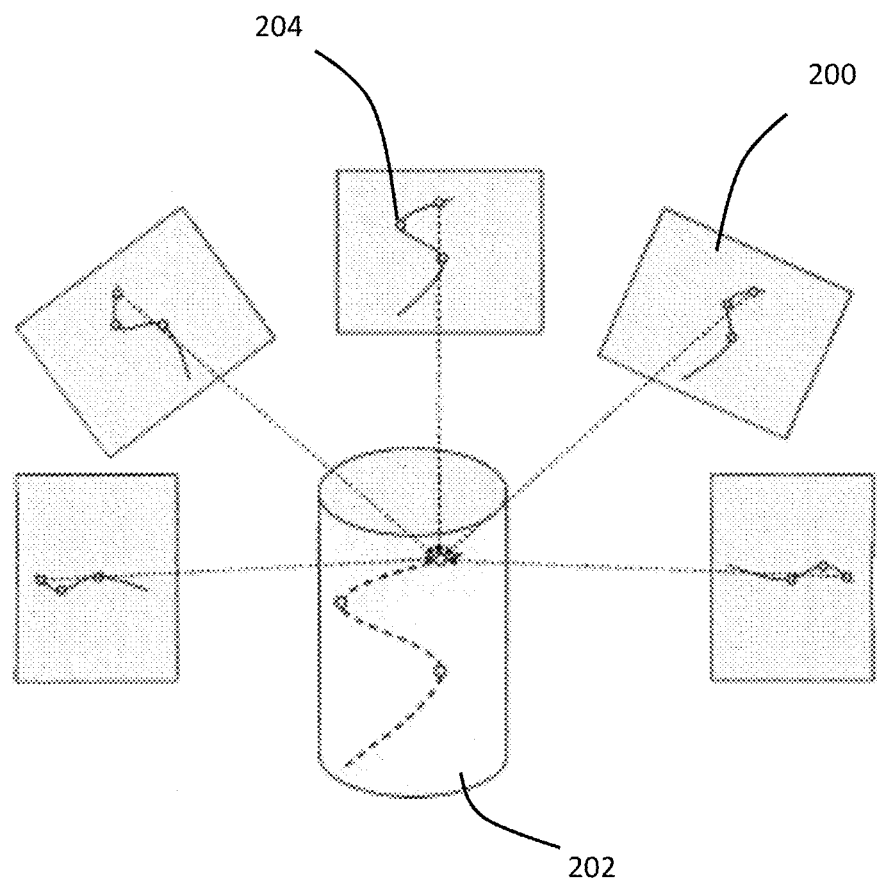
FIG. 2 illustrates and exemplary three dimensional (3D) reconstruction of a tracking marker after segmentation from a two dimensional (2D) image.

FIG. 2 illustrates a 3D reconstruction of one of the tracking markers after segmentation in the n 2D projection images. The embodiment of FIG. 2 shows five 2D projection images 200 of the tracked medical tool 202 generated by the processor of the imaging system. Three tracking markers 204, for example, are visible in the five 2D projection images 200. If vector paths do not intersect after 3D reconstruction of a tracking marker after segmentation in the 2D projection images, a 3D point with a minimal distance to all vector paths is calculated and taken as a best approximation of a 3D tracking marker position in a first coordinate system (e.g., the image coordinate system). Other methods (e.g., averaging) may be used to determine the 3D tracking marker position in the first coordinate system.

In act 108, a 3D position of the tracked medical tool and/or 3D positions of the tracking markers within a second coordinate system (e.g., the global coordinate system) are determined by the processor based on, for example, signals emitted by the tracking devices of the tracking markers (e.g., EM signals emitted by the tracking coils of the tracking devices). The 3D positions of the tracking markers within the second coordinate system may be determined at a plurality of time points corresponding to the plurality of time points at which the 2D projection images are generated. In other words, the 2D projection images may be generated and the 3D positions of the tracking markers within the second coordinate system may be determined simultaneously. In one embodiment, the 3D position for each of the tracking markers within the second coordinate system may be calculated by averaging the determined 3D positions within the second coordinate system for the tracking marker over the plurality of time points.

In act 110, the processor registers the 3D position data for the tracking markers within the first coordinate system from act 106 with the 3D position data for the tracking markers within the second coordinate system from act 108. The registration may be a point based registration. The point based registration may include translation, rotation, etc. of one data set relative to the other. The resultant registration may be saved to a memory of the imaging system for future tracking of the tracked medical tool within the patient.

Figure 3:
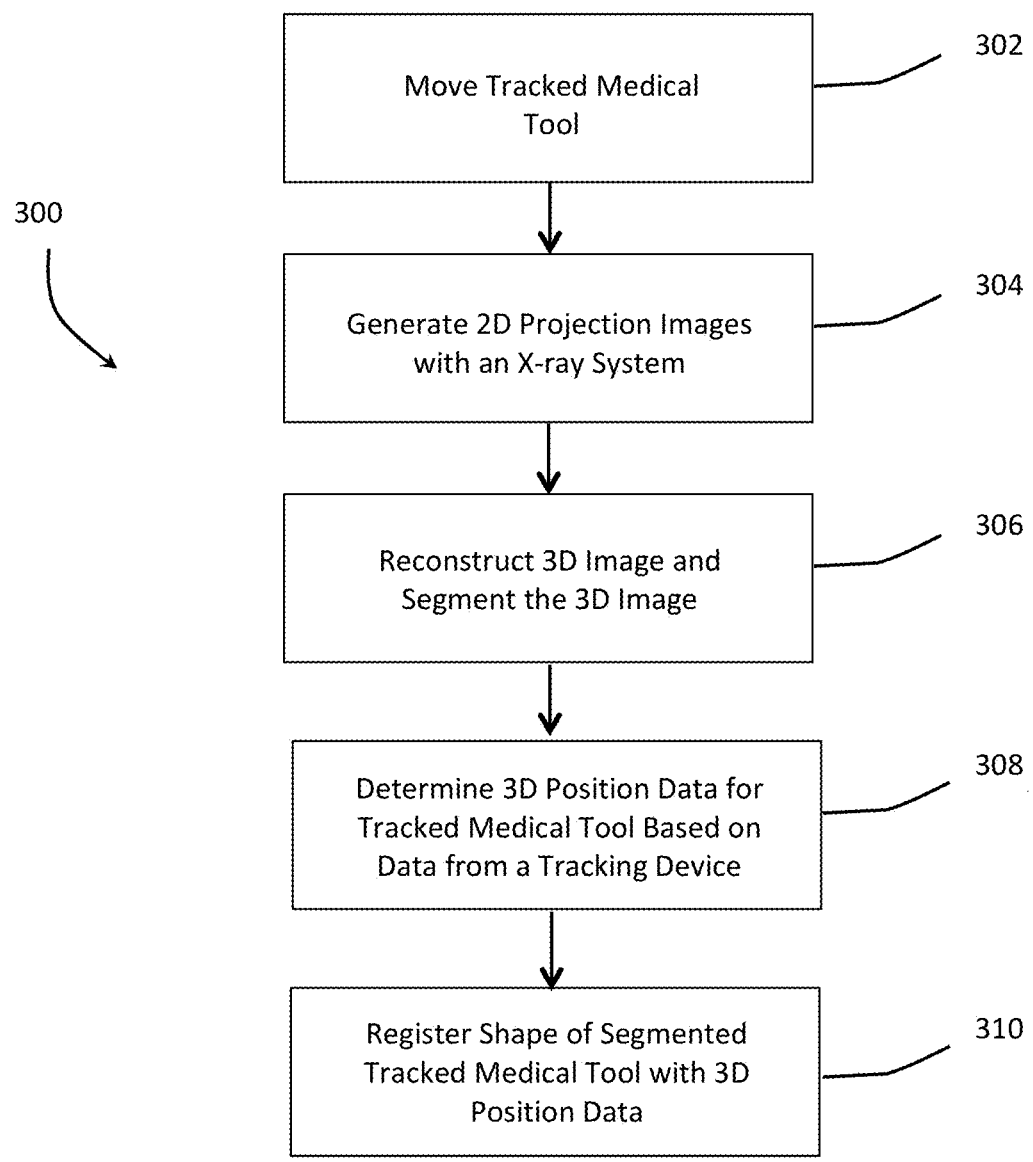
FIG. 3 is a flow chart diagram of a second embodiment of a method for registering a tracked medical tool and an imaging system.

FIG. 3 is a flow chart diagram of an embodiment of a method 300 for registering a tracked medical tool and an imaging system. The tracked medical tool may include two or more tracking markers. The two or more tracking markers may not be visible in an image generated by the imaging system. The method illustrated by FIG. 3 may be used when the two or more tracking markers are not visible in one or more of the images generated by the imaging system.

In act 302, the tracked medical tool is moved through a body of a patient into a field of view of the imaging system. In act 304, a number, n, of 2D projection images (e.g., two or more projection images) are generated by a processor of the imaging system. For each projection image of the n 2D projection images, the geometry of the imaging system is known. In one embodiment, hundreds of 2D projection images are generated by the processor the imaging system.

In act 306, the processor reconstructs a 3D image from the n 2D projection images. In one embodiment, filtering is applied to the 2D projection images to isolate the representations of the tracked medical tool in the 2D projection images. A representation of the tracked medical tool is segmented from the reconstructed 3D image. The representation of the tracked medical tool may be automatically segmented from the reconstructed 3D image. Alternatively, a user of the imaging system may identify a region within the reconstructed image to be segmented using an input device, and the processor may segment the representation of the tracked medical tool based on the identified region received from the input device.

In act 308, a 3D position of the tracked medical tool and/or 3D positions of the tracking markers within a second coordinate system (e.g., the global coordinate system) are determined by the processor based on, for example, signals emitted by the tracking devices of the tracking markers (e.g., EM signals emitted by the tracking coils of the tracking devices). The 3D positions of the tracking markers within the second coordinate system may be determined at a plurality of time points corresponding to the plurality of time points at which the 2D projection images are generated. In other words, the 2D projection images may be generated and the 3D positions of the tracking markers within the second coordinate system may be determined simultaneously. In one embodiment, the 3D position for each of the tracking markers within the second coordinate system may be calculated by averaging the determined 3D positions within the second coordinate system for the tracking marker over the plurality of time points.

In act 310, the shape of the representation of the tracked medical tool segmented from the reconstructed 3D image in act 306 is registered (e.g., matched and/or fit) with the determined 3D positions of the tracking markers within the second coordinate system from act 308. For example, one of the data sets (e.g., the segmented representation of the tracked medical tool) is registered (e.g., translated, rotated, etc.) to the other of the data sets (e.g., the determined 3D positions of the tracking markers within the second coordinate system). The resultant registration may be saved to a memory of the imaging system for future tracking of the tracked medical tool within the patient.

Figure 4:
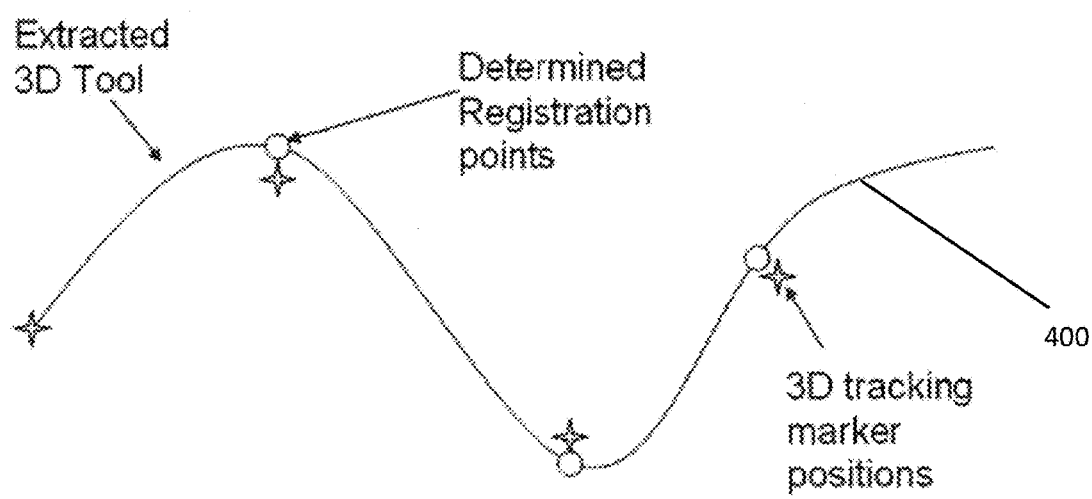
FIG. 4 illustrates an exemplary registration of a segmented representation of the tracked medical tool with a dataset based on data received from the tracked medical tool.

FIG. 4 illustrates a representation 400 of the tracked medical tool segmented from a reconstructed 3D image (e.g., from act 306) displayed with determined 3D positions of the tracking markers within the second coordinate system (e.g., from act 308). In the embodiment shown in FIG. 4, a guidewire is represented. Other tracked medical tools may be represented.

The registration of act 310 may include the processor determining a least squares match of the shape of the determined 3D positions of the tracking markers within the second coordinate system. The registration may thus be between the least squares curve and the segmented representation of the tracked tool. Other matches may be used.

Error sources such as large metallic devices and the human body may disturb the magnetic field used with the tracking devices, for example. Accordingly, such error sources may affect the accuracy of the tracking devices. Distortions may be assumed to be homogeneous throughout the tracked medical tool. 3D correction vectors may be determined for each of the tracked marker positions based on a comparison between the determined least squares curve and the segmented representation of the tracked tool.

Figure 5:
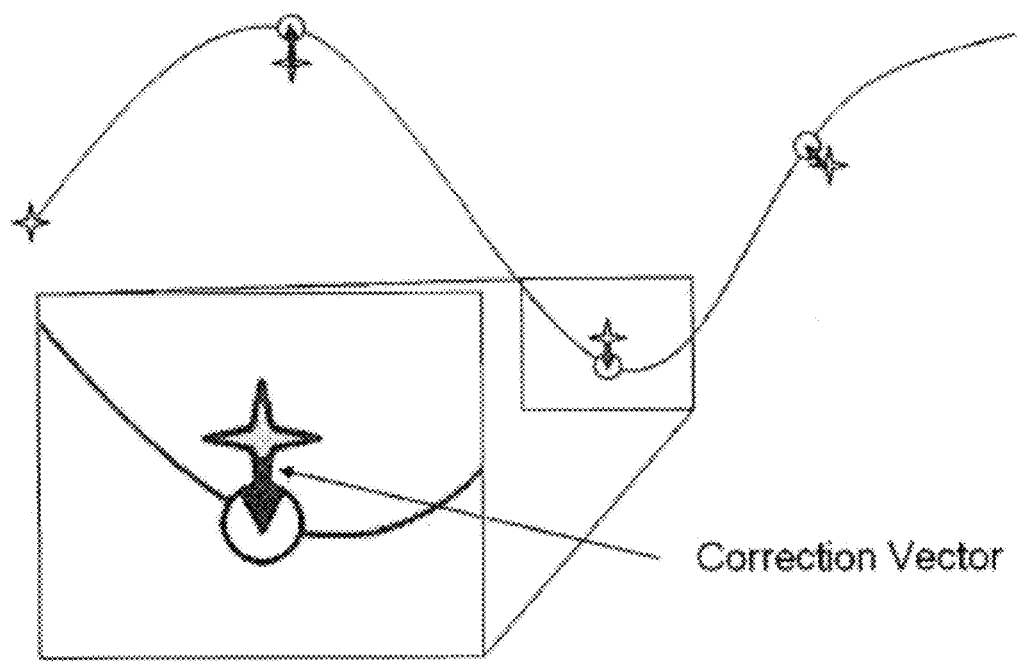
FIG. 5 illustrates exemplary correction vectors determined between corresponding points of the segmented representation of the tracked medical tool with the dataset based on the data received from the tracked medical tool.

FIG. 5 illustrates exemplary correction vectors determined between corresponding points of the segmented representation of the tracked medical tool with the data set generated based on data received from the tracked medical tool (e.g., the tracking devices). Correction vectors are determined between corresponding points. The determined correction vectors may be stored in a memory of the imaging system for future calibrations. The determined correction vectors are applied to the tracked marker positions and may be extrapolated throughout the tracked medical tool.

Figure 6:
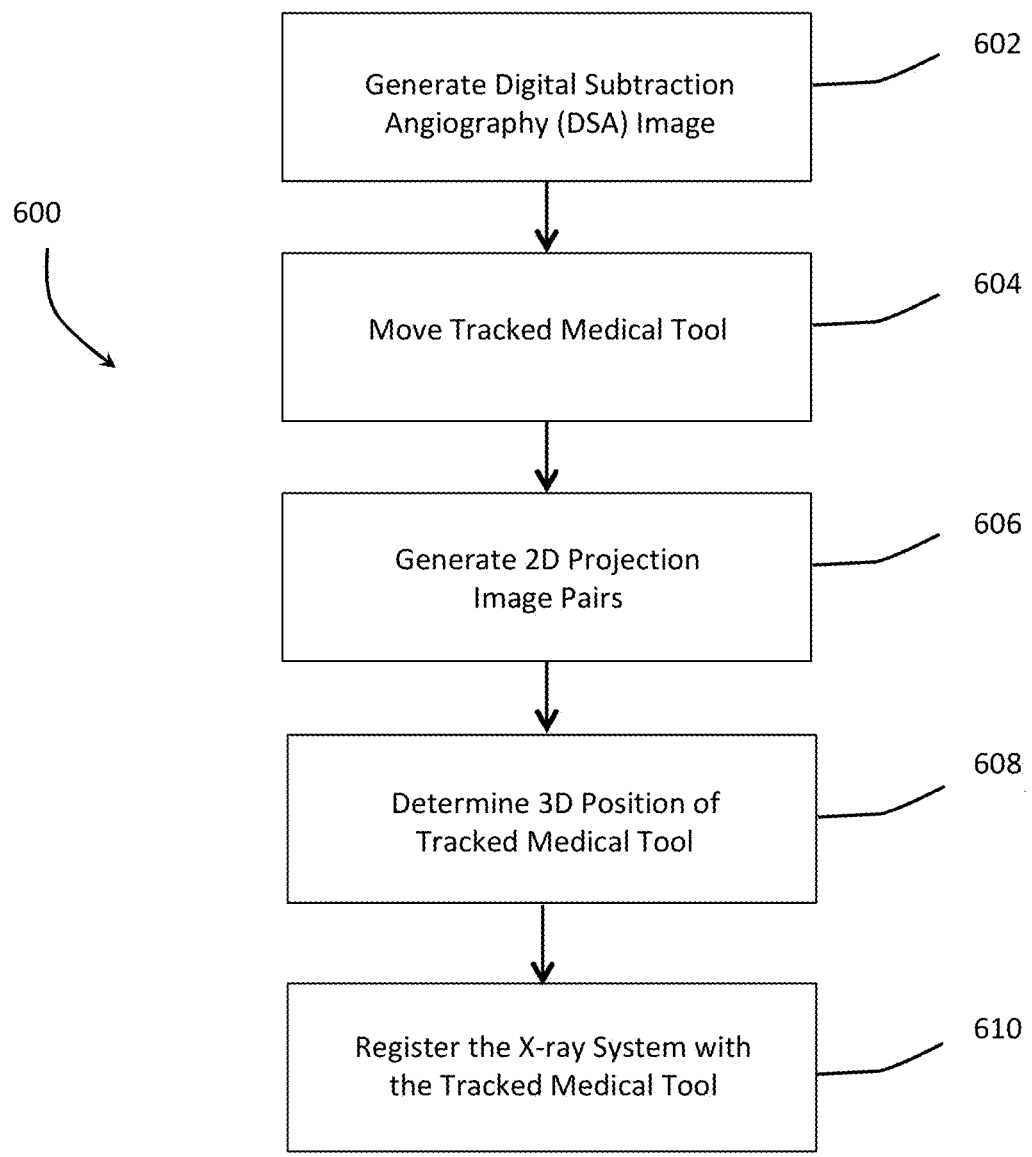
FIG. 6 is a flow chart diagram of a third embodiment of a method for registering a tracked medical tool and an imaging system.

FIG. 6 is a flow chart diagram of an embodiment of a method 600 for registering a tracked medical tool and an imaging system. The method of FIG. 6 may be used when the tracked medical tool includes a single visible tracking marker. The imaging system may include a biplane X-ray system (e.g., a biplane fluoroscopy system) for the embodiment of FIG. 6. The biplane X-ray system generates images in two different planes (e.g., a vertical plane and a horizontal plane) at the same time. The biplane X-ray system includes, for example, two X-ray sources and two corresponding detectors that are rotatable around the patient.

In act 602, a 3D digital subtraction angiography (DSA) image is generated by the processor. Generation of the 3D DSA image includes the imaging system generating a plurality of 2D projection images of the tracked medical tool inside the body of the patient. The plurality of 2D projection images include 2D projection images generated based on data received when a contrast agent is injected into the patient and 2D projection images generated based on data received when the contrast agent is not injected into the patient. The processor reconstructs a 3D mask image or a pre-contrast image based on the 2D projection images that do not include the contrast agent, and reconstructs a 3D contrast image based on the 2D projection images that do include the contrast agent. The processor generates the DSA image based on a subtraction of the 3D mask image from the 3D contrast image.

In act 604, the tracked medical tool is advanced to a position visible in a field of view of the biplane imaging system. The position of the patient may change, but the tracked medical tool is positioned in the 3D DSA structure (e.g., using a 3D/2D overlay).

In act 606, 2D projection image pairs (e.g., images in two planes) are generated by a processor of the imaging system. The 2D projection image pairs are generated while the tracked medical tool moves through the field of view of the biplane imaging system. Any number of 2D projection image pairs may be generated. Image data is received from the two detectors of the imaging system, for example, and the processor generates the 2D projection image pairs based on the received image data. For each projection image, the geometry of the imaging system is known.

A 3D position of the tracked medical tool and/or 3D positions of the tracking marker within a second coordinate system (e.g., the global coordinate system) are determined by the processor based on, for example, signals emitted by the tracking devices of the (e.g., EM signals emitted by the tracking coils of the tracking devices). The 3D positions of the tracking markers within the second coordinate system may be determined at a plurality of time points corresponding to the plurality of time points at which the 2D projection images are generated. In other words, the 2D projection images may be generated and the 3D positions of the tracking markers within the second coordinate system may be determined simultaneously.

In act 608, the processor determines a 3D position of the tracked medical tool or the tracking marker within a first coordinate system (e.g., the image coordinate system) for each of the generated 2D projection image pairs. This determination includes triangulating the 3D position of the tracked medical tool or the tracking marker inside the 3D DSA image based on marker positions extracted (e.g., segmented) from the generated 2D projection image pairs.

Figure 7:
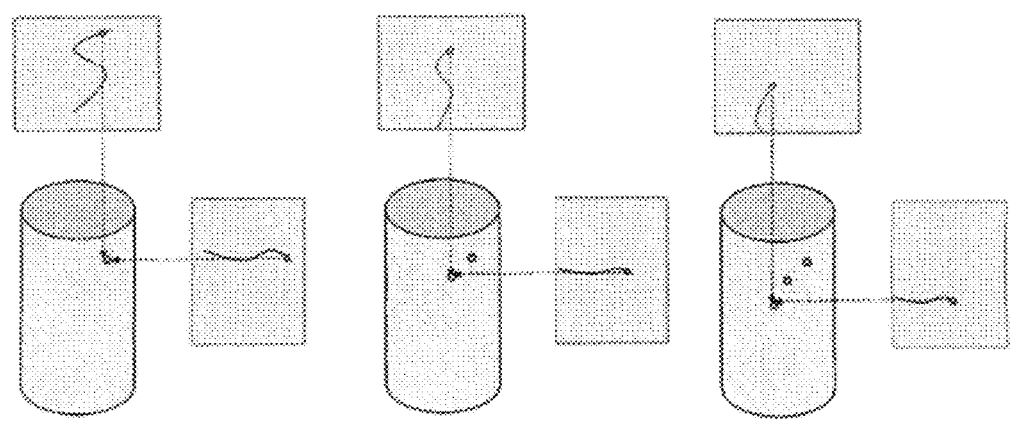
FIG. 7 illustrates motion of the tracked medical tool in 2D with the tracking marker visible.

FIG. 7 illustrates motion of the tracked medical tool in 2D with the tracking marker visible. The extracted tracking marker position is triangulated in 3D and recorded in a memory of the imaging system. For each point recorded this way, a tracking position is recorded.

If the tracking marker position is clearly visible and has been extracted in the 2D projection images, the corresponding triangulated 3D positions are used for registration. If the tracking marker positions are not clearly visible, the known shape of the tracked medical tool (e.g., with marker position) is fit to the reconstructed/triangulated toll, and the tracking marker position is correlated. In one embodiment, the fitting includes a constraint deformation of the tracked medical tool (e.g., from a starting point of a straight line to the reconstructed shape).

In act 610, the processor registers the 3D position data for the tracking marker within the first coordinate system from act 608 with the 3D position data for the tracking marker within the second coordinate system from act 606. The registration may be a point based registration. The point based registration may include translation, rotation, etc. of one data set relative to the other. The resultant registration may be saved to a memory of the imaging system for future tracking of the tracked medical tool within the patient.

Figure 8:
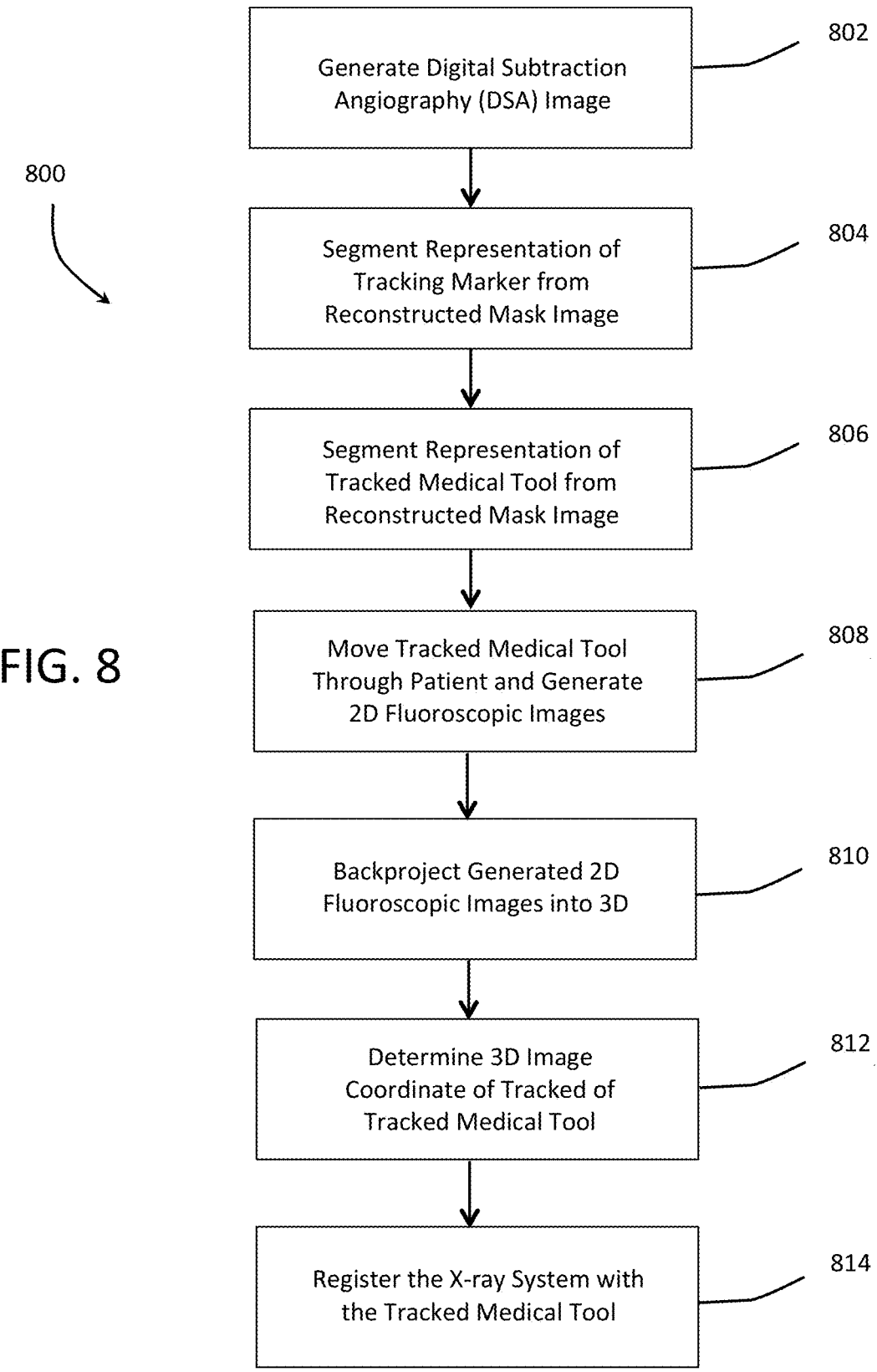
FIG. 8 is a flow chart diagram of a fourth embodiment of a method for registering a tracked medical tool and an imaging system.

FIG. 8 is a flow chart diagram of an embodiment of a method 800 for registering a tracked medical tool and an imaging system. The method of FIG. 8 may be used when the tracked medical tool includes a single visible tracking marker. The imaging system may include a monoplane X-ray system (e.g., a monoplane fluoroscopy X-ray system) for the embodiment of FIG. 8. The monoplane X-ray system may include, for example, a C-arm with an X-ray source and a detector attached to different sides of the C-arm. The X-ray source and the detector may be rotatable around the patient using the C-arm.

In act 802, a 3D digital subtraction angiography (DSA) image is generated by the processor. Generation of the 3D DSA image includes the imaging system generating a plurality of 2D projection images of the tracked medical tool inside the body of the patient. The plurality of 2D projection images include 2D projection images generated based on data received when a contrast agent is injected into the patient and 2D projection images generated based on data received when the contrast agent is not injected into the patient. The processor reconstructs a 3D mask image or a pre-contrast image based on the 2D projection images that do not include the contrast agent, and reconstructs a 3D contrast image based on the 2D projection images that do include the contrast agent. The processor generates the DSA image based on a subtraction of the 3D mask image from the 3D contrast image.

In act 804, a representation of the tracking marker is segmented from the reconstructed 3D mask image within a first coordinate system (e.g., the image coordinate system). The representation of the tracking marker may be automatically segmented from the reconstructed 3D mask image. Alternatively, a user of the imaging system may identify a region within the reconstructed 3D mask image to be segmented using an input device, and the processor may segment the representation of the tracking marker based on the identified region received from the input device.

A 3D position of the tracked medical tool and/or 3D position of the tracking marker within a second coordinate system (e.g., the global coordinate system) is determined by the processor based on, for example, signals emitted by the tracking devices of the (e.g., EM signals emitted by the tracking coils of the tracking devices). The 3D position of the tracking marker within the second coordinate system may be determined at one or more time points corresponding to the one or more time points at which the 2D projection images are generated. In other words, the 2D projection images may be generated and the 3D positions of the tracking markers within the second coordinate system may be determined simultaneously.

In act 806, a representation of the tracked medical tool is segmented (e.g., extracted) from the reconstructed 3D mask image. The representation of the tracked medical tool segmented from the reconstructed 3D mask image may be altered. For example, a tool diameter of the segmented representation of the tracked medical tool may be increased. In one embodiment, the tool diameter is increased by blurring or in-plane diameter dilation. The segmented representation of the tracked medical tool may be altered in other ways.

In act 808, the tracked medical tool is moved through the body of the patient within a field of view of the imaging system. A number of 2D fluoroscopic images are generated by the processor of the imaging system based on image data received at the detector of the imaging system, as the tracked medical tool moves through the field of view of the imaging system. For each of the 2D fluoroscopic images, the geometry of the imaging system is known. Any number of 2D fluoroscopic images may be generated.

A 3D position of the tracked medical tool and/or a 3D position of the tracking marker within a second coordinate system (e.g., the global coordinate system) is determined by the processor based on, for example, signals emitted by the tracking devices of the (e.g., EM signals emitted by the tracking coils of the tracking devices). The 3D position of the tracking marker within the second coordinate system may be determined at a plurality of time points corresponding to the plurality of time points at which 2D fluoroscopic images are generated. In other words, the 2D fluoroscopic images may be generated and the 3D position of the tracking marker within the second coordinate system may be determined simultaneously.

In act 810, the processor backprojects the 2D fluoroscopic images of the moving tool into the 3D using the altered segmented representation of the tracked medical tool as a constraining volume. In one embodiment, if the tracking marker is identifiable in the 2D fluoroscopic images and a representation of the tracking marker may be segmented from the 2D fluoroscopic images, only the representation of the tracking marker is backprojected.

In act 812, the processor determines a 3D image coordinate of the tracked medical tool and/or the tracking marker within the first coordinate system. This determination includes the processor determining an intersection point of the backprojected 2D object (e.g., the moving tool or the tracking marker) with the altered segmented representation of the tracked medical tool.

Figure 9:
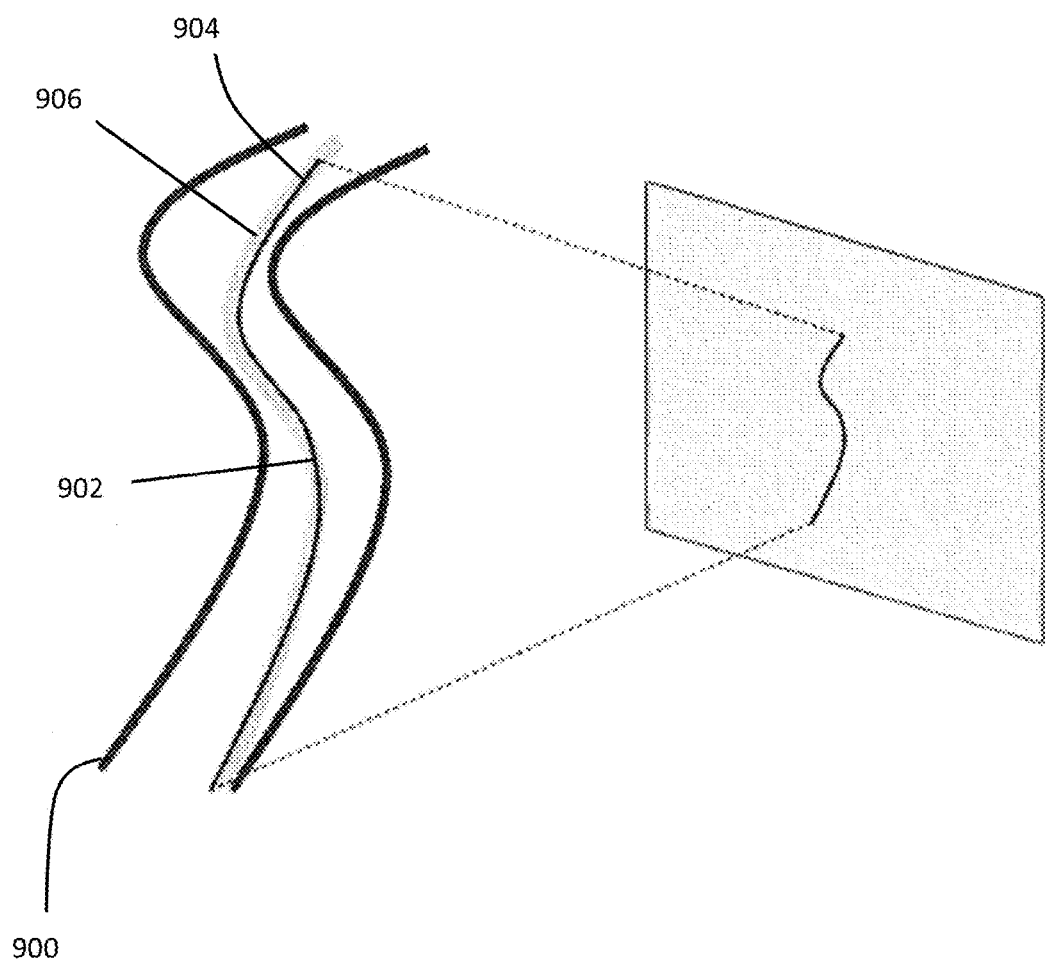
FIG. 9 illustrates a backprojection of a segmented representation of the tracked medical tool into a blurred tool reconstruction.

FIG. 9 shows a backprojection of a segmented representation of the tracked medical tool into a blurred tool reconstruction. Reconstructed vascular structure 900 acts as a constraining volume, and an intersection point 902 of the backprojected 2D object 904 with the altered segmented representation of the tracked medical tool 906 defines the 3D image coordinate of the tracked medical tool. In one embodiment, if there is more than one intersection coordinate for the tracked medical tool 906 or the tracking marker, the center of mass may be used as a first approximation of the tool/marker position.

In act 814, the processor registers the 3D position data for the tracking marker within the first coordinate system from act 812 with the 3D position data for the tracking marker within the second coordinate system from act 808. The registration may be a point based registration. The point based registration may include translation, rotation, etc. of one data set relative to the other. The resultant registration may be saved to a memory of the imaging system for future tracking of the tracked medical tool within the patient.

Figure 10:
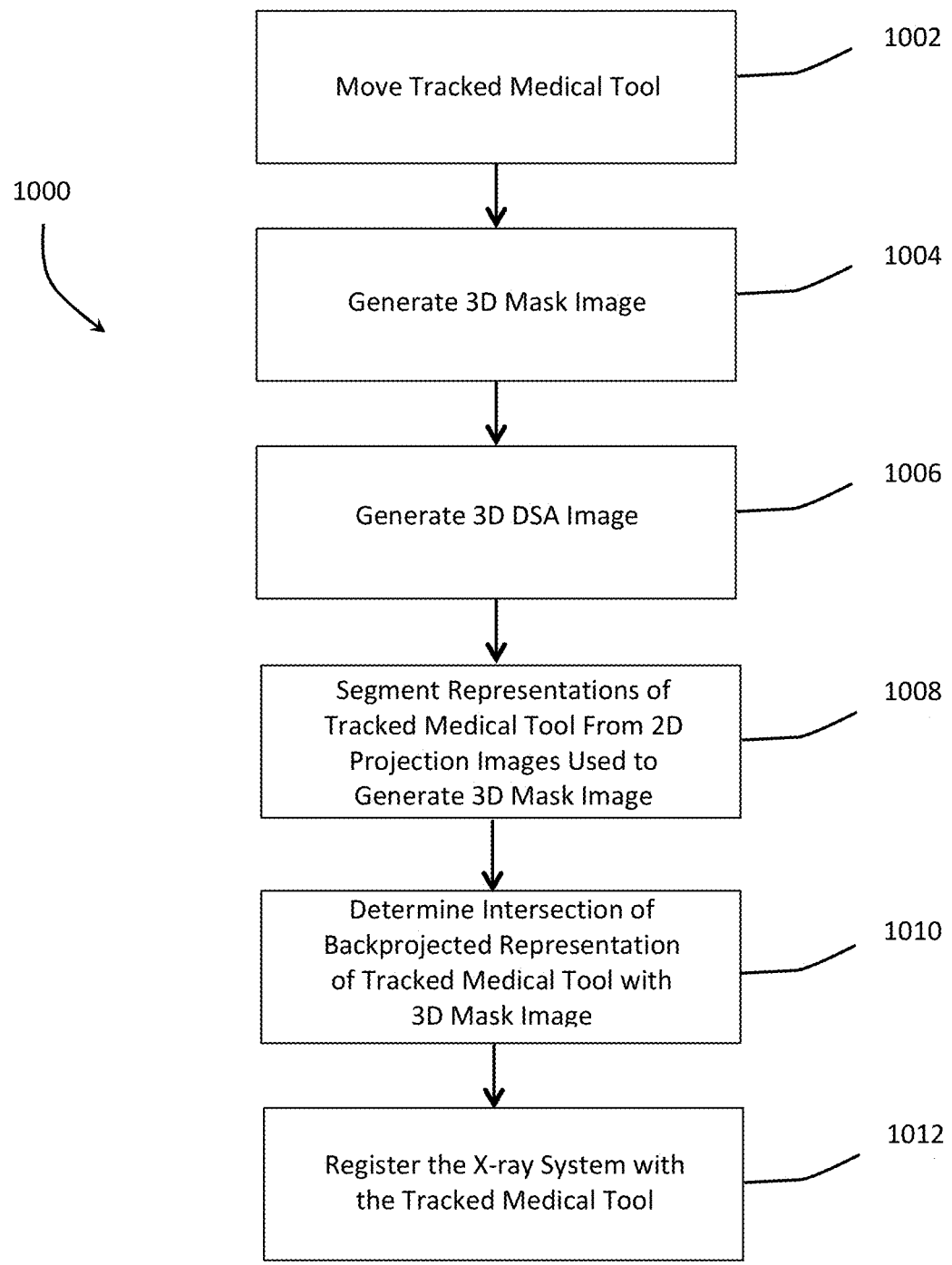
FIG. 10 is a flow chart diagram of a fifth embodiment of a method for registering a tracked medical tool and an imaging system.

FIG. 10 is a flow chart diagram of one embodiment of a method 1000 for registering a tracked medical tool and an imaging system. The method of FIG. 10 may be used when the tracked medical tool includes a single visible tracking marker. The imaging system may include a monoplane X-ray system (e.g., a monoplane fluoroscopy X-ray system) for the embodiment of FIG. 10. The monoplane X-ray system may include, for example, a C-arm with an X-ray source and a detector attached to different sides of the C-arm. The X-ray source and the detector may be rotatable around the patient using the C-arm. Other imaging systems may be used.

In act 1002, a tracked medical tool is moved into a field of view of a 3D image acquisition. The tracked medical tool may be positioned within the field of view such that the tracked medical tool may move distally within the field of view. The tracked medical tool may be positioned within the field of view such that the tracked medical tool does not overlay any vasculature of interest.

In act 1004, the processor generates a 3D mask image in a 3D mask run. The 3D mask image is generated during pull back of the tracked medical tool. Generation of the 3D mask image includes the imaging system generating 2D projection images of the tracked medical tool inside the body of the patient when no contrast agent is injected into the patient. The processor reconstructs the 3D mask image based on the 2D projection images that do not include the contrast agent. The 3D mask image includes a blurred reconstruction of the tracked medical tool due to the motion of the tracked medical tool during the acquisition.

A 3D position of the tracked medical tool and/or 3D position of the tracking marker within a second coordinate system (e.g., the global coordinate system) is determined by the processor based on, for example, signals emitted by the tracking devices of the (e.g., EM signals emitted by the tracking coils of the tracking devices). The 3D position of the tracked medical tool within the second coordinate system may be determined at a plurality of time points corresponding to the plurality of time points at which the 2D projection images are generated during the 3D mask run. In other words, the 2D projection images may be generated and the 3D position of the tracked medical tool within the second coordinate system may be determined simultaneously.

In act 1006, the processor generates a 3D DSA image. A plurality of 2D projection images are generated based on data received from the detector during imaging when a contrast agent is injected into the patient. The processor reconstructs a 3D contrast image based on the 2D projection images that include the contrast agent. The processor generates the DSA image based on a subtraction of the 3D mask image from the 3D contrast image.

In act 1008, a representation of the tracked medical tool is segmented (e.g., extracted) from each 2D projection image generated in the 3D mask run (e.g., with the tracked medical tool moving from frame to frame). The representations of the tracked medical tool are backprojected into 3D.

In act 1010, an intersection of the backprojected tracked medical tool from act 1008 with the blurred reconstruction of the tracked medical tool of act 1004 is determined. If the tracking marker is clearly visible in 2D, the 3D intersection coordinate may be determined and used as the 3D position of the tracked medical tool and/or the tracking marker within a first coordinate system (e.g., the imaging coordinate system). If the tracking marker is not clearly visible in 2D, a method similar to the embodiment illustrated in FIG. 8 may be used to determine the 3D position of the tracking marker and/or the tracked medical tool. If there is more than one intersection coordinate for the tracked medical tool and/or the tracking marker, the center of mass may be used as a first approximation of the tracked medical tool/tracking marker.

In act 1012, the processor registers the 3D position data for the tracking marker within the first coordinate system from act 1010 with the 3D position data for the tracking marker within the second coordinate system from act 1004. The registration may be a point based registration. The point based registration may include translation, rotation, etc. of one data set relative to the other. The resultant registration may be saved to a memory of the imaging system for future tracking of the tracked medical tool within the patient.

Figure 11:
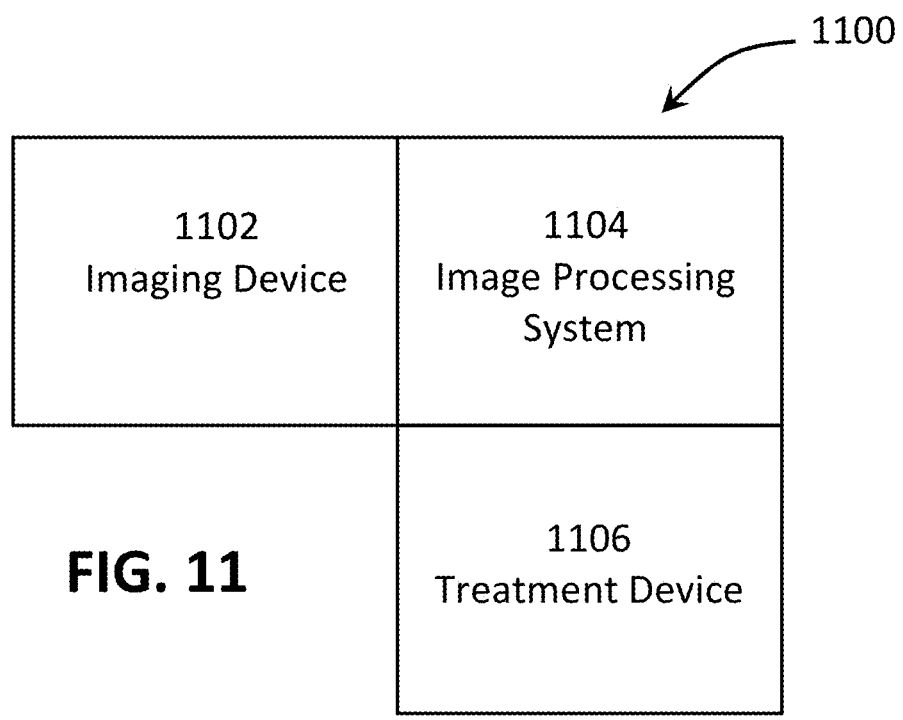
FIG. 11 shows one embodiment of a system for registering an image system and a therapy system.

FIG. 11 shows one embodiment of a system (e.g., a registration system) for registering an image system and a therapy system. The registration system may be used in the methods described above. The registration system 1100 may include one or more imaging devices 1102 (e.g., an imaging device), one or more image processing systems 1104 (e.g., an image processing system), and one or more treatment devices 1106 (e.g., a treatment device). A dataset representing a two-dimensional (2D) or a three-dimensional (3D) (e.g., volumetric) region may be acquired using the one or more imaging devices 1102 and the image processing system 1104 (e.g., an imaging system). The 2D dataset or the 3D dataset may be obtained contemporaneously with the panning and/or execution of a medical treatment procedure or at an earlier time. Additional, different or fewer components may be provided.

In one embodiment, the imaging system 1102, 1104 is, for example, a cone-beam X-ray system. The cone-beam X-ray system 1102, 1104 may generate 2D projection images, 3D images reconstructed from the 2D projection images, fluoroscopic images, DSA images, or a combination thereof. The cone-beam X-ray system 1102, 1104 may generate any number of other images. The imaging system 1102, 1104 may be used to provide accurate registration between the imaging system 1102, 1104 and the treatment 1106 device such that a trackable device of the treatment device 1106 may be moved within a body of a patient without any additional live imaging such as, for example, fluoroscopy or ultrasound after registration. For example, the image processing system 1104 is a workstation for registering data generated by a tracking device of the treatment device 1106 with data generated by the cone-beam X-ray system 1102, 1104. In other embodiments, the imaging system 1102, 1104 may include, for example, a medical workstation, a computed tomography (CT) system, an ultrasound system, a positron emission tomography (PET) system, an angiography system, a fluoroscopy, an x-ray system, any other now known or later developed imaging system, or a combination thereof. The workstation 1104 receives data representing or images of the patient (e.g., including at least part of the body of the patient and the treatment device 106) generated by the imaging device 1102.

The treatment device 1106 may be registered with the imaging system 1102, 1104 using the imaging system 1102, 1104 and a tracking device of the treatment device. The treatment device 1106 may be any number of treatment devices including, for example, a tracked endovascular tool such as a guidewire or a catheter. The tracked endovascular tool 1106 may include one or more trackable markers (e.g., markers). The markers may include, for example tracking coils. The markers may thus act as the tracking device for the tracked endovascular tool 1106. The therapy system 1100 may include more or fewer components.

Figure 12:
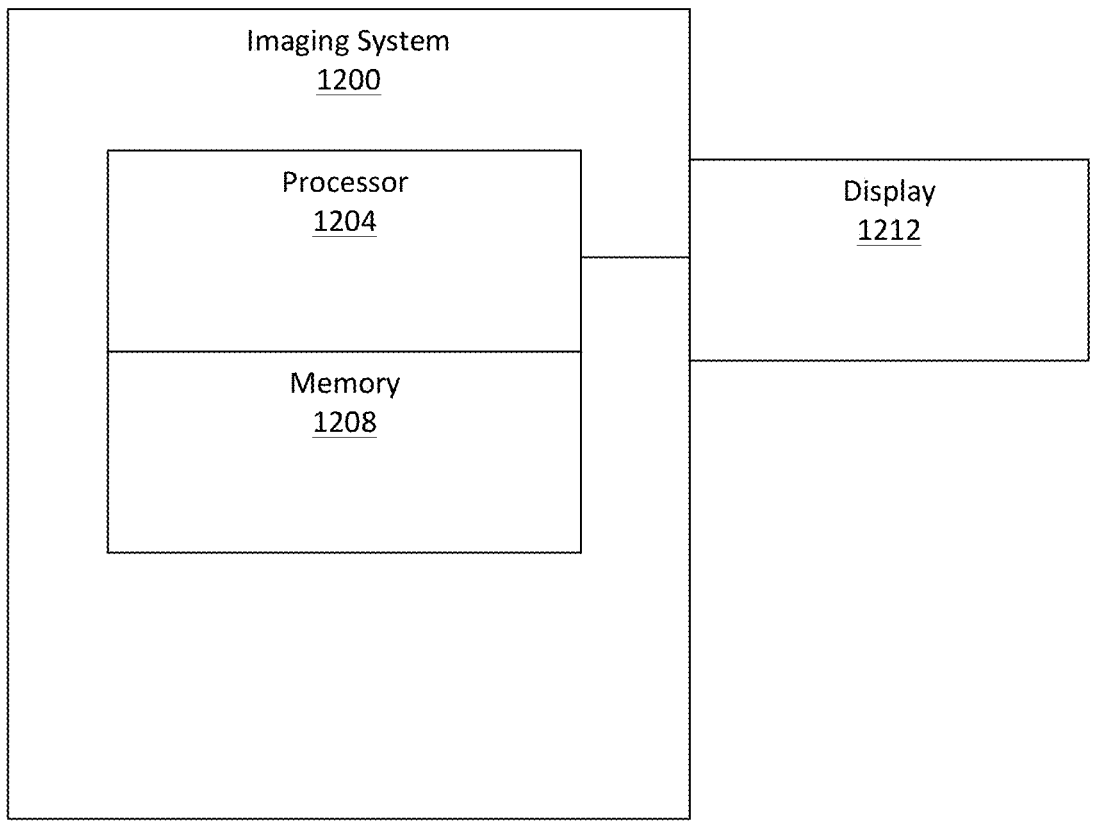
FIG. 12 shows one embodiment of an imaging system for registering data generated by the imaging system with data generated by a tracking device of a medical device or tool.

FIG. 12 shows one embodiment of an imaging system 1200 for registering data generated by the imaging system 1200 with data generated by a tracking device of a medical device or tool (e.g., a marker of the medical device or tool). The imaging system 1200 may correspond to the imaging system 1102, 1104 and may be used in the methods described above. The system 1200 is an X-ray imaging system (e.g., a cone-beam X-ray system), but may be a computer, workstation, database, server, or other system. The system 1200 includes a processor 1204, a memory 1208, and a display 1212. In other embodiments, the system 1200 may include additional, different, or fewer components. For example, the system 1200 may include an x-ray source and detector.

The memory 1208 is a buffer, cache, RAM, removable media, hard drive, magnetic, optical, database, or other now known or later developed memory. The memory 1208 is a single device or group of two or more devices. The memory 1208 is shown within the system 1200, but may be outside or remote from other components of the system 1200, such as a database or PACS memory.

The memory 1208 stores medical imaging data (e.g., frames of medical imaging data). Any type of medical imaging data (e.g., fluoroscopy, magnetic resonance, CT, etc., imaging data) may be stored. For example, a sequence of frames of fluoroscopy imaging data is stored. As another example, a sequence of frames of DSA imaging data is stored. The sequence is acquired over seconds or minutes. The medical images are of a region including, for example, a vessel, a guidewire or catheter, and/or markers (e.g., a marker on the catheter). The catheter, for example, may be introduced during acquisition of the sequence or may already be in place during the acquisition. The vessel may or may not include a guide wire for placement of the catheter. The data includes a representation of one or more markers for the catheter, for example. Alternatively, the medical image data is transferred to the processor 1204 from another device with or without storage in the memory 1208.

For real-time imaging, the medical data bypasses the memory 1208, is temporarily stored in the memory 1208, or is loaded from the memory 1208. Real-time imaging may allow delay of a fraction of seconds, or even seconds, between acquisition of data and imaging. For example, real-time imaging is provided by generating images of the sequence substantially simultaneously with the acquisition of the data by scanning. To allow better visualization of the catheter (e.g., catheters with less metal or radio opaque materials), for example, an enhanced catheter image may be generated. In alternative embodiments, the image data is stored in the memory 1208 from a previous imaging session and used for detecting markers and/or generating catheter enhanced images.

The memory 1208 is additionally or alternatively a non-transitory computer readable storage medium with processing instructions. The memory 1208 stores data representing instructions executable by the programmed processor 1204 for marker detection in medical imaging of a catheter. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and non-volatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 1204 is a general processor, digital signal processor, graphics processing unit, application specific integrated circuit, field programmable gate array, digital circuit, analog circuit, combinations thereof, or other now known or later developed device for processing frames of data for medical images. The processor 1204 is a single device, a plurality of devices, or a network. For more than one device, parallel or sequential division of processing may be used. Different devices making up the processor 1204 may perform different functions, such as a marker detector and a separate device for generating a catheter enhanced image. In one embodiment, the processor 1204 is a control processor or other processor of a medical diagnostic imaging system, such as a cone-beam X-ray imaging system processor. The processor 1204 operates pursuant to stored instructions to perform various acts described herein, such as obtaining frames of image data, determining a plurality of candidate markers, automatically initializing a detector, tracking one or more markers, providing an image of the catheter based on the tracking, registering, or combinations thereof.

The processor 1204 is configured to perform any or all of the above-described acts (e.g., the acts illustrated in FIGS. 1-10). The processor 1204 is configured to obtain a plurality of frames of image data. The processor 1204 is configured to determine a plurality of candidate markers for the catheter, for example, in the plurality of frames of image data. The processor 1204 is configured to detect one or more candidate markers from the plurality of candidate markers. The processor 1204 is configured to automatically initialize the detection using a subset of frames of the image data from the plurality of frames of image data. The processor 1204 is configured to detect based, at least in part, on the automatic initialization. The processor 1204 is configured to detect in real-time.

The display 1212 is a CRT, LCD, plasma, projector, printer, or other output device for showing an image. The display 1212 displays an image of two or more markers. A catheter enhanced image with markers enhanced and/or highlighted may be displayed. An image of marker characteristics may be displayed, such as displaying a value representing the distance between markers. In other embodiments, the markers are not displayed, are displayed to indicate the location, or are merely displayed as part of an image without highlighting or enhancement.

Prior to the methods detailed above, the registration between an intra-operative dataset and a tracking mechanism was performed using specific registration and reference markers positioned outside the patient or required a work intensive integration with an interventional imaging device. With the registration provided by the present embodiments, the registration may be performed online, the registration does not require any registration markers positioned on the patient and inside a field of view of the interventional imaging device, or a fixed connection to a C-arm of the interventional imaging device. Accordingly, the registration markers are close to the region of interest, which may provide a higher tracking accuracy. In summary, the registration provided by the present embodiments, provides for faster registration and higher tracking accuracy than the registration methods of the prior art. Further, there is no need to change the acquired field of view, and there is no extra registration step to be performed by the user.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for registration of an endovascular device with an X-ray system, the endovascular device comprising a tracking device, the method comprising:
   receiving image data from the X-ray system at a plurality of time points, the image data comprising image data representing at least a portion of the endovascular device in a first coordinate system as the endovascular device moves within or through the first coordinate system;
   receiving tracking data generated by the tracking device at the plurality of time points, the tracking data representing a global position of the endovascular device in a second coordinate system, the second coordinate system being a global coordinate system;
   registering, by a processor, the second coordinate system with the first coordinate system based on the received image data and the received tracking data at the plurality of time points,
   wherein the tracking device comprises tracking coils configured to generate an electromagnetic (EM) signal comprising the tracking data representing the global position of the endovascular device in the second coordinate system.

2. The method of claim 1, further comprising:
   generating, by the processor, a plurality of projection images based on the received image data from the X-ray system; and
   calculating, by the processor, positions of one or more markers of the tracking device within the first coordinate system, the first coordinate system being a three-dimensional (3D) image coordinate system,
   wherein the registering comprises performing point based registration between the calculated positions of the one or more markers of the tracking device and the received tracking data from the tracking device.

3. The method of claim 2, wherein the calculating comprises:
   generating a three-dimensional (3D) image based on the plurality of generated projection images and segmenting the one or more markers from the 3D image; or
   segmenting the one or more markers of the tracking device from the plurality of projection images and reconstructing a 3D image of the one or more markers.

4. The method of claim 1, further comprising:
generating, by the processor, a plurality of projection images based on the received image data from the X-ray system;
generating a three-dimensional (3D) image based on the plurality of generated projection images, the generated 3D image representing at least the portion of the endovascular device; and
segmenting at least the portion of the endovascular device from the 3D image,
wherein receiving the tracking data comprises receiving data representing positions of one or more tracking markers of the tracking device in the second coordinate system from the tracking device, and
wherein the registering comprises matching the segmented portion of the endovascular device from the 3D image to the received data representing the positions of the one or more tracking markers of the tracking device.

5. The method of claim 4, further comprising filtering the plurality of projection images, the filtering isolating the endovascular device within the plurality of projection images.

6. The method of claim 1, wherein the received image data is received first image data, and
wherein the method further comprises:
receiving second image data from the X-ray system or another X-ray system, the second image data representing an object in which the endovascular device is disposable, the received second image data comprising image data representing the object with a contrast agent injected and image data representing the object with no contrast agent injected; and
generating a three dimensional (3D) digital subtraction angiography (DSA) image of the object based on the received second image data.

7. The method of claim 6, further comprising:
generating one or more fluoroscopic image pairs of at least the portion of the endovascular device based on the received first image data, fluoroscopic images of each of the one or more generated fluoroscopic image pairs being in different planes;
triangulating a 3D position of one or more markers of the tracking device within the 3D DSA image based on the one or more generated fluoroscopic image pairs,
wherein the registering comprises performing point based registration between the triangulated 3D position of the one or more markers of the tracking device and the received tracking data from the tracking device.

8. The method of claim 6, further comprising:
generating, by the processor, a plurality of fluoroscopic images based on the received first image data; and
segmenting a representation of an electromagnetic (EM) trackable marker of the tracking device or a representation of the endovascular device from each fluoroscopic image of the plurality of fluoroscopic images.

9. The method of claim 8, wherein receiving the second image data comprises receiving second image data that represents the object and at least the portion of the endovascular device, at least a portion of the second image data representing the EM trackable marker, the received tracking data comprising tracking data representing a position of the EM trackable marker in the second coordinate system at the plurality of time points and another time point, and
wherein the generating of the 3D DSA image comprises generating a 3D DSA image of the object and at least the portion of the endovascular device based on the received second image data.

10. The method of claim 9, further comprising:
generating a 3D mask image of the object and at least the portion of the endovascular device based on the received second image data;
segmenting a representation of the EM trackable marker and a representation of the endovascular device from the 3D mask image;
matching the representation of the EM trackable marker segmented from the 3D mask image with the tracking data representing the position of the EM trackable marker in the second coordinate system at the other time point;
altering the representation of the endovascular device segmented from the 3D mask image, the altering comprising increasing a diameter of the representation of the endovascular device segmented from the 3D mask image;
backprojecting the representation of the EM trackable marker or the representation of the endovascular device segmented from each fluoroscopic image of the plurality of fluoroscopic images into the altered segmented representation of the endovascular device; and
determining a position of at least the portion of the endovascular device in the first coordinate system, the determining comprising identifying one or more intersection points of the backprojected representation of the EM trackable marker or the backprojected representation of the endovascular device with the altered segmented representation of the endovascular device,
wherein the registering comprises performing point based registration between the one or more intersection points and a portion of the received tracking data from the tracking device.

11. The method of claim 1, wherein receiving the image data comprises receiving image data representing an object in which the endovascular device is disposable, the received image data comprising image data representing the object with a contrast agent injected and image data representing the object with no contrast agent injected,
wherein the method further comprises:
generating a plurality of projection images based on the received image data from the X-ray system;
generating a 3D mask image of the object and at least the portion of the endovascular device based on the plurality of generated projection images, the generated 3D mask image including a reconstruction of the endovascular device;
generating a three dimensional (3D) digital subtraction angiography (DSA) image based on the received image data and the generated 3D mask image.

12. The method of claim 11, further comprising:
segmenting a representation of the endovascular device from each projection image of the plurality of projection images;
backprojecting the segmented representation of the endovascular device into 3D; and
determining an intersection of the backprojected segmented representation of the endovascular device with the reconstruction of the endovascular device,
wherein the registering comprises performing point based registration between the determined intersection and the received tracking data from the tracking device.

13. A system for registration of a tracked tool with an X-ray system, the tracked tool comprising a tracking device, the system comprising:

an X-ray system configured to generate image data representing at least a portion of the tracked tool in a first coordinate system as the tracked tool moves within or through the first coordinate system; and a processor configured to:
receive tracking data generated by the tracking device while the X-ray system generates the image data, the tracking data representing a global position of the tracked tool in a second coordinate system, the second coordinate system being a global coordinate system;
register the second coordinate system with the first coordinate system based on the received image data and the received tracking data,
wherein the tracking device comprises tracking coils configured to generate an electromagnetic (EM) signal comprising the tracking data representing the global position of the tracked tool in the second coordinate system.

14. The system of claim 13, wherein the tracked tool comprises a guidewire or a catheter.

15. The system of claim 13, wherein the tracking device further comprises RFID chips, center-of-mass fiducials, an electromagnetically trackable marker, or a combination thereof.

16. The system of claim 13, wherein the X-ray system comprises a biplane fluoroscopy imaging system.

17. In a non-transitory computer-readable storage medium that stores instructions executable by one or more processors for registration of data generated by a tracked medical tool with image data generated by an X-ray system, the tracked medical tool comprising a tracking device, the instructions comprising:
receiving image data from the X-ray system at a plurality of time points, the image data comprising image data representing at least a portion of the tracked medical tool in a first coordinate system as the tracked medical tool moves within or through the first coordinate system;
receiving an electromagnetic (EM) signal comprising tracking data generated by tracking coils of the tracking device of the tracked medical tool at the plurality of time points, the tracking data representing a global position of the tracked medical tool in a second coordinate system, the second coordinate system being a global coordinate system;
registering the second coordinate system with the first coordinate system based on the received image data and the received tracking data representing the global position of the tracked medical tool in the second coordinate system at the plurality of time points.

18. The non-transitory computer-readable storage medium of claim 17, wherein the instructions further comprise:
generating a plurality of projection images based on the received image data from the X-ray system; and
calculating positions of one or more markers of the tracking device within the first coordinate system, the first coordinate system being a three-dimensional (3D) image coordinate system,
wherein the registering comprises performing point based registration between the calculated positions of the one or more markers of the tracking device and the received tracking data from the tracking device, and
wherein the calculating comprises:
generating a three-dimensional (3D) image based on the plurality of generated projection images and segmenting the one or more markers from the 3D image; or
segmenting the one or more markers of the tracking device from the plurality of projection images and reconstructing a 3D image of the one or more markers.

19. The non-transitory computer-readable storage medium of claim 17, further comprising:
generating a plurality of projection images based on the received image data from the X-ray system;
filtering the plurality of projection images, the filtering isolating the tracked medical tool within the plurality of projection images;
generating a three-dimensional (3D) image based on the plurality of generated projection images, the generated 3D image representing at least the portion of the tracked medical tool; and
segmenting at least the portion of the tracked medical tool from the 3D image,
wherein receiving the tracking data comprises receiving data representing positions of one or more tracking markers of the tracking device in the second coordinate system from the tracking device, and
wherein the registering comprises matching the segmented portion of the tracked medical tool from the 3D image to the received data representing the positions of the one or more tracking markers of the tracking device.

20. The non-transitory computer-readable storage medium of claim 17, wherein the received image data is received first image data,
wherein the method further comprises:
receiving second image data from the X-ray system or another X-ray system, the second image data representing an object in which the tracked medical tool is disposable, the received second image data comprising image data representing the object with a contrast agent injected and image data representing the object with no contrast agent injected; and
generating a three dimensional (3D) digital subtraction angiography (DSA) image of the object based on the received second image data;
generating one or more fluoroscopic image pairs of at least the portion of the tracked medical tool based on the received first image data, fluoroscopic images of each of the one or more generated fluoroscopic image pairs being in different planes; and
triangulating a 3D position of one or more markers of the tracking device within the 3D DSA image based on the one or more generated fluoroscopic image pairs,
wherein the registering comprises performing point based registration between the triangulated 3D position of the one or more markers of the tracking device and the received tracking data from the tracking device.

* * * * *